United States Patent [19]

Uhr et al.

[11] Patent Number: 5,767,137

[45] Date of Patent: Jun. 16, 1998

[54] 1,3,2-BENZODITHIAZOL-1-OXIDES AS MICROBIOCIDES

[75] Inventors: Hermann Uhr, Krefeld; Franz Kunisch, Odenthal-Glöbusch; Peter Wachtler, Köln; Martin Kugler, Leichlingen; Joachim Mittendorf, Wuppertal, all of Germany

[73] Assignee: Bayer Aktiengesellschaft, Leverkusen, Germany

[21] Appl. No.: 663,160

[22] PCT Filed: Jan. 26, 1995

[86] PCT No.: PCT/EP95/00283

§ 371 Date: Aug. 1, 1996

§ 102(e) Date: Aug. 1, 1996

[87] PCT Pub. No.: WO95/21526

PCT Pub. Date: Aug. 17, 1995

[30] Foreign Application Priority Data

Feb. 8, 1994 [DE] Germany ............ 44 03 838.0

[51] Int. Cl.⁶ .......... A01N 43/82; A01N 43/78; C07D 277/62; C07D 277/16
[52] U.S. Cl. .......... 514/360; 548/123
[58] Field of Search .......... 548/123; 514/360, 514/338, 234.2; 544/134; 546/268.4; 424/407, 414, 415, 416, 417; 106/18.32, 18.33

[56] References Cited

U.S. PATENT DOCUMENTS 5,131,939 7/1992 Hsu .......... 71/67

5,140,018 8/1992 Klein et al. .......... 514/63

FOREIGN PATENT DOCUMENTS 475 123    3/1992   European Pat. Off.
1 531 431 11/1978  United Kingdom.

OTHER PUBLICATIONS

Klein et al., Synthesis and Antifungal Activity of 1,3,2-Benzodithiazol.S-Oxides, Journal of Medicinal Chemistry, vol. 37, No. 5, pp. 572–578, Aug. 1993.

Primary Examiner—John M. Ford
Assistant Examiner—Pavanaram K. Sripada
Attorney, Agent, or Firm—Sprung Kramer Schaefer & Briscoe

[57] ABSTRACT

A description is given of novel and know 1,3,2-benzodithiazole 1-oxides of the formula (I)

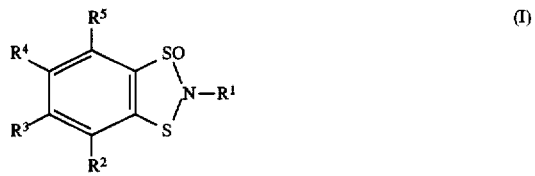

and of their preparation and use for protecting industrial materials against infestation by microorganisms.

3 Claims, No Drawings

1,3,2-BENZODITHIAZOL-1-OXIDES AS MICROBIOCIDES

This application is a 371 OF PCT/EP95/00283 Jan. 26, 1995.

The invention relates to the microbicidal use of 1,3,2-benzodithiazole 1-oxides, to novel 1,3,2-benzodithiazole 1-oxides and to processes for their preparation.

It is already known that certain 1,3,2-benzodithiazole 1-oxides have an antimycotic action in pharmaceutical compositions (see U.S. Pat. No. 5,140,018).

Furthermore, structurally similar N-alkyl-benz[1,2] isothiazolin-3-ones and their use in the protection of materials are known (see e.g. DE-A 4 027 378, GB 1 531 431, EP 18 100). The activity and breadth of action of these compounds, however, is not always completely satisfactory, especially at low concentrations. Surprisingly, the 1,3,2-benzodithiazole 1-oxides according to the invention have not only a greater breadth of action but also a markedly higher activity.

It has been found that the 1,3,2-benzodithiazole 1-oxides—some of which are known—of the general formula (I)

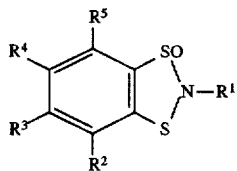

in which
  $R^1$ represents hydrogen, optionally substituted alkyl, alkoxy, alkenyl, alkinyl, cycloalkyl, aryl, heteroaryl or aralkyl, or heteroarylalkyl, and
  $R^2$ $R^3$ $R^4$ and $R^5$ each independently of one another represent hydrogen, halogen, alkyl, halogenoalkyl, alkoxy, halogenoalkoxy, alkylthio, halogenoalkylthio, dialkylamino, nitro or cyano
are suitable as microbiocides for protecting industrial materials.

A general definition of the 1,3,2-benzodithiazole 1-oxides which can be used in accordance with the invention is given by the formula (I). Preference is given to compounds of the formula (I) in which
  $R^1$ represents hydrogen, straight-chain and branched alkyl having 1 to 18 carbon atoms, straight-chain or branched alkenyl having 2 to 18 carbon atoms or straight-chain or branched alkinyl having 2 to 18 carbon atoms which is optionally substituted one or more times by identical or different substituents consisting of halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, (alkoxy)-carbonyl having 1 to 6 carbon atoms, amino which is optionally substituted by identical or different substituents consisting of alkyl or aryl, optionally substituted phenoxy or pyridyloxy, nitro or cyano,
  and represents cycloalkyl consisting of 1 to 4 interconnected ring systems having 3 to 18 carbon atoms which is optionally substituted one or more times by identical or different substituents consisting of halogen, alkyl having 1 to 4 carbon atoms, halogenoalkyl having 1 to 4 carbon atoms and 1 to 5 identical or different halogen atoms, alkoxy having 1 to 4 carbon atoms, halogenoalkoxy having 1 to 4 carbon atoms and 1 to 5 identical or different halogen atoms, alkylthio having 1 to 4 carbon atoms, halogenoalkylthio having 1 to 4 carbon atoms and 1 to 5 identical or different halogen atoms, nitro or cyano,
  and represents aryl which is optionally substituted from one to five times by halogen, alkyl having 1 to 10 carbon atoms, halogenoalkyl having 1 to 8 carbon atoms and 1 to 8 identical or different halogen atoms, alkoxy having 1 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino having straight-chain or branched alkyl radicals having 1 to 6 carbon atoms, dialkylamino having identical or different; straight-chain or branched alkyl radicals each having 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano,
  and represents aralkyl in which the alkyl radical is straight or branched and consists of 1 to 8 carbon atoms and aryl preferably represents phenyl which is optionally substituted from one to four times by identical or different substituents consisting of halogen, alkyl having 1 to 6 carbon atoms, halogenoalkyl having 1 to 6 carbon atoms and 1 to 6 identical or different halogen atoms, alkoxy having 1 to 6 carbon atoms, halogenoalkoxy having 1 to 6 carbon atoms and 1 to 6 identical or different halogen atoms, alkylthio having 1 to 6 carbon atoms, halogenoalkylthio having 1 to 6 carbon atoms and 1 to 6 identical or different halogen atoms, amino, monoalkylamino having straight-chain and branched alkyl radicals having 1 to 6 carbon atoms, dialkylamino having identical or different, straight-chain or branched alkyl radicals each having 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano,
  $R^2$, $R^3$, $R^4$ and $R^5$ each independently of one another represent hydrogen, halogen, alkyl having 1 to 6 carbon atoms, halogenoalkyl having 1 to 6 carbon atoms and 1 to 6 identical or different halogen atoms, alkoxy having 1 to 6 carbon atoms, halogenoalkoxy having 1 to 6 carbon atoms and 1 to 6 identical or different halogen atoms, alkylthio having 1 to 6 carbon atoms, halogenoalkylthio having 1 to 6 carbon atoms and 1 to 6 identical or different halogen atoms, dialkylamino having identical or different, straight-chain or branched alkyl radicals each having 1 to 6 carbon atoms, nitro or cyano.

Particular preference is given to compounds of the formula (I) in which
  $R^1$ represents hydrogen, straight-chain or branched alkyl having 1 to 14 carbon atoms, straight-chain or branched alkenyl having 2 to 14 carbon atoms or straight-chain or branched alkinyl having 2 to 14 carbon atoms which is optionally substituted from one to four times by identical or different substituents consisting of fluorine, chlorine, alkoxy having 1 to 5 carbon atoms, halogenoalkoxy having 1 to 5 carbon atoms and 1 to 5 fluorine and/or chlorine atoms, alkylthio having 1 to 5 carbon atoms, halogenoalkylthio having 1 to 5 carbon atoms and 1 to 5 fluorine and/or chlorine atoms, acyl having 1 to 5 carbon atoms, acyloxy having 1 to 5 carbon atoms, alkoxycarbonyl having 1 to 5 carbon atoms, amino which is optionally substituted by identical or different substituents consisting of alkyl having 1 to 4 carbon atoms and/or phenyl, phenoxy or pyridyloxy, nitro or cyano, and represents cycloalkyl consisting of 1 to 3 ring systems having 3 to 14 carbon atoms which is optionally substituted from one to four times by identical or different substituents consisting of fluorine/chlorine, alkyl having 1 to 4 carbon atoms, alkoxy having 1 to 4 carbon atoms, alkylthio having 1 to 4 carbon atoms, nitro or cyano, and represents aryl which is optionally substituted from one to four times by fluorine, chlorine, alkyl having 1 to 8 carbon atoms, halogenoalkyl having 1 to 6 carbon atoms and 1 to 6 fluorine and/or chlorine atoms, alkoxy having 1 to 8 carbon atoms, halogenoalkoxy having 1 to 6 carbon atoms and 1 to 6 fluorine and/or chlorine atoms, alkylthio having 1 to 8 carbon atoms, halogenoalkylthio having 1 to 6 carbon atoms and 1 to 6 fluorine and/or chlorine atoms, amino, monoalkylamino having alkyl radicals of 1 to 4 carbon atoms, dialkylamino having identical or different alkyl radicals each having 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano, and represents aralkyl in which the alkyl radical is straight or branched and consists of 1 to 8 carbon atoms and aryl represents phenyl which is optionally substituted from one to four times by fluorine, chlorine, alkyl having 1 to 4 carbon atoms, halogenoalkyl having 1 to 4 carbon atoms and 1 to 4 fluorine and/or chlorine atoms, alkoxy having 1 to 4 carbon atoms, halogenoalkoxy having 1 to 4 carbon atoms and 1 to 4 fluorine and/or chlorine atoms, alkylthio having 1 to 4 carbon atoms, halogenoalkylthio having 1 to 4 carbon atoms and 1 to 4 fluorine and/or chlorine atoms, amino, monoalkylamino having alkyl radicals of 1 to 4 carbon atoms, dialkylamino having identical or different alkyl radicals each having 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano, $R^2$, $R^3$, $R^4$ and $R^5$ each independently of one another represent hydrogen, chlorine, fluorine, alkyl having 1 to 4 carbon atoms, halogenoalkyl having 1 to 4 carbon atoms and 1 to 6 fluorine and/or chlorine atoms, alkoxy having 1 to 4 carbon atoms, halogenoalkoxy having 1 to 4 carbon atoms and 1 to 6 fluorine and/or chlorine atoms, alkylthio having 1 to 4 carbon atoms, halogenoalkylthio having 1 to 4 carbon atoms and 1 to 6 fluorine and/or chlorine atoms, dialkylamino having identical or different, straight-chain or branched alkyl radicals each having 1 to 6 carbon atoms, nitro or cyano.

The 1,3,2-benzodithiazole 1-oxides of the formula (I) which can be used in accordance with the invention are in some cases known (cf. U.S. Pat. No. 5,140,018) and can be prepared by analogous processes.

Novel 1,3,2-benzodithiazole 1-oxides are those of the formula (Ia)

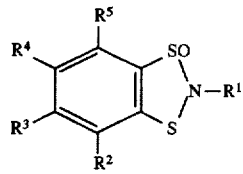

in which $R^1$ represents hydrogen, straight-chain or branched alkyl having 13 to 18 carbon atoms, straight-chain or branched alkenyl or alkinyl having 17 to 18 carbon atoms and represents straight-chain or branched alkyl having 1 to 18 carbon atoms which is substituted one or more times by identical or different substituents consisting of halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, amino which is optionally substituted by identical or different substituents consisting of alkyl or aryl, optionally substituted phenoxy or pyridyloxy, nitro or cyano, and represents straight-chain or branched alkenyl or alkinyl of 1 to 18 carbon atoms which is substituted one or more times by halogen, alkoxy having 1 to 6 carbon atoms, halogenoalkoxy having 1 to 6 carbon atoms and 1 to 9 identical or different halogen atoms, alkylthio having 1 to 6 carbon atoms, halogenoalkylthio having 1 to 6 carbon atoms and 1 to 9 identical or different halogen atoms, acyl having 1 to 6 carbon atoms, acyloxy having 1 to 6 carbon atoms, (alkoxy)-carbonyl having 1 to 6 carbon atoms, amino which is optionally substituted by identical or different substituents consisting of alkyl or aryl, optionally substituted phenoxy or pyridyloxy, nitro or cyano, and represents cycloalkyl consisting of 1 to 4 interconnected ring systems having 3 to 18 carbon atoms which is substituted one or more times by identical or different substituents consisting of halogen, alkyl having 1 to 4 carbon atoms, halogenoalkyl having 1 to 4 carbon atoms and 1 to 5 identical or different halogen atoms, alkoxy having 1 to 4 carbon atoms, halogenoalkoxy having 1 to 4 carbon atoms and 1 to 5 identical or different halogen atoms, alkylthio having 1 to 4 carbon atoms, halogenoalkylthio having 1 to 4 carbon atoms and 1 to 5 identical or different halogen atoms, nitro or cyano, and represents aryl which is substituted from one to five times by alkyl having 5 to 10 carbon atoms, halogenoalkyl having 5 to 8 carbon atoms and 1 to 8 identical or different halogen atoms, alkoxy having 5 to 10 carbon atoms, halogenoalkoxy having 1 to 8 carbon atoms and 1 to 8 identical or different halogen atoms, alkylthio having 1 to 10 carbon atoms, halogenoalkylthio having 1 to 8 carbon atoms and 1 to 8 identical or different halogen atoms, amino, monoalkylamino and straight-chain and branched alkyl radicals having 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano, and represents aralkyl in which the alkyl radical is straight or branched and consists of 5 to 8 carbon atoms and aryl represents phenyl which is substituted from one to four times by identical or different substituents consisting of halogenoalkoxy having 1 to 6 carbon atoms and 1 to 6 identical or different halogen atoms, alkylthio having 1 to 6 carbon atoms, halogenoalkylthio having 1 to 6 carbon atoms and 1 to 6 identical or different halogen atoms, amino, monoalkylawmino having straight-chain and branched alkyl radicals having 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano.

$R^2$, $R^3$, $R^4$ and $R^5$ each independently of one another represent hydrogen, halogen, alkyl having 1 to 6 carbon atoms, halogenoalkyl having 1 to 6 carbon atoms and 1 to 6 identical or different halogen atoms, alkoxy having 1 to 6 carbon atoms, halogenoalkoxy having 1 to 6 carbon atoms and 1 to 6 identical or different halogen atoms, alkylthio having 1 to 6 carbon atoms, halogenoalkylthio having 1 to 6 carbon atoms and 1 to 6 identical or different halogen atoms, dialkylamino having identical or different, straight-chain or branched alkyl radicals each having 1 to 6 carbon atoms, nitro or cyano.

The known and novel 1,3,2-benzodithiazole 1-oxides of the general formula (I)
in which
$R^1$, $R^2$, $R^3$, $R^4$, $R^5$ have the meaning given above
are obtained if compounds of the general formula (II)

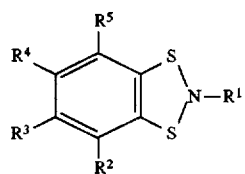
(II)

in which
$R^1$, $R^2$, $R^3$, $R^4$ and $R^5$ have the meaning given above
are reacted by analogous processes (see U.S. Pat. No. 5,140,018) with oxidizing agents, optionally in the presence of diluents.

The compounds with the general formula (II) likewise show biological effects and are suitable as microbicides for protecting industrial materials.

All customary oxidizing agents can be used for the oxidation; mention may be made here by way of example of organic peroxides, for example m-chloroperbenzoic acid (mCPBA) or monoperoxyphthalic acid magnesium salt hexahydrate (MMPP) or organic oxidizing agents, for example pyridinium chlorochromate (PCC), pyridine-$SO_3$, pyridinium dichromate (PDC) or t-butyl hypochloride, but also mild inorganic oxidizing agents such as $H_2O_2$, sodium iodate, sodium perborate or oxone manganese dioxide.

The reaction temperatures can be varied within a relatively large temperature range. The reaction is in general carried out at between $-30°$ C. and $+100°$ C., preferably between $-10°$ C. and $+60°$ C. The reactions are preferably carried out in the presence of diluents. Suitable diluents are water and organic solvents which are also attacked by the oxidizing agents. These include, preferably, hydrocarbons such as toluene, xylene or hexane, chlorinated hydrocarbons such as chlorobenzene, chloroform, methylene chloride, ethers such as methyl tert-butyl ether, or nitriles, such as acetonitrile.

The known and novel benzodithiazoles of the general formula (II)

in which
$R^1$, $R^2$, $R^3$, $R^4$ and $R^5$ have the meaning given above
are obtained if sulphenyl chlorides of the general formula (III)

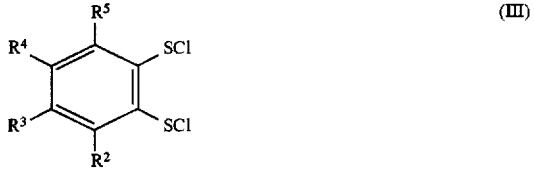
(III)

in which
$R^2$, $R^3$, $R^4$ and $R^5$ have the meaning given above
are reacted by analogous processes (see U.S. Pat. No. 5,140,180; C. H. Chen, J. Heterocyclic. Chem., 16, 183 (1979)) with amines of the general formula (IV)

$H_2N-R^1$ (IV)

in which
$R^1$ has the meaning given above,
if desired in the presence of acid-binding agents and if desired in the presence of diluents.

In this process the reaction temperatures can be varied within a relatively large temperature range. The process is in general carried out at between $-30°$ C. and $+100°$ C., preferably between $-10°$ C. and $+50°$ C. The reactions are optionally carried out in the presence of acid-binding agents, in which case all customary acid-binding agents can be used. These include, preferably, tertiary amines such as triethylamine and pyridine; alkali metal hydroxides, such as sodium hydroxide and potassium hydroxide, and alkali metal carbonates and alkali metal halogen carbonates, such as potassium carbonate and sodium hydrogen carbonate.

Suitable diluents, which are optionally used, are all inert organic solvents. These include, preferably, hydrocarbons such as toluene, xylene or hexane; chlorinated hydrocarbons such as chlorobenzene and chloroform; ketones such as acetone; ethers such as tetrahydrofuran, diethyl ether, methyl tert-butyl ether and dioxane; nitriles such as acetonitrile.

The known and novel sulphenyl chlorides of the general formula (III)
in which
$R^2$, $R^3$, $R^4$ and $R^5$ have the meaning given above
are obtained if dithiols of the formula (V)

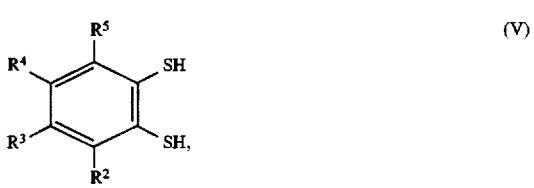
(V)

are reacted with chlorine gas in the presence of diluents.

Diluents employed are preferably chlorinated hydrocarbons, for example carbon tetrachloride, chloroform, methylene chloride or 1,2-dichloroethane. The temperatures can be varied within a large range; the process is in general carried out at between $-30°$ C. and $+40°$ C., preferably at temperatures below $20°$ C.

In an alternative procedure, however, the sulphenyl chlorides can under identical conditions also be obtained by chlorinating the disulfide compounds with the general formulae (VI) and (VII) and their positional isomers (see e.g. E. Kühle, The Chemistry of the sulfenic acids, Georg Thieme Verlag, Stuttgart 1973).

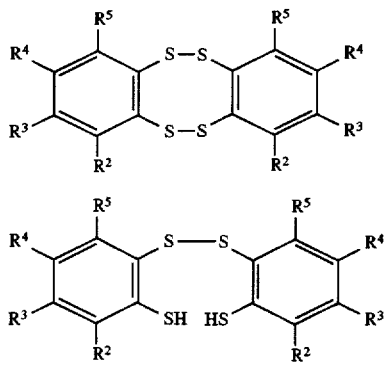
(VI)

(VII)

Another alternative for the preparation of the sulphenyl chlorides of the formula (III) consists in the chlorination of compounds of the general formula (VIII)

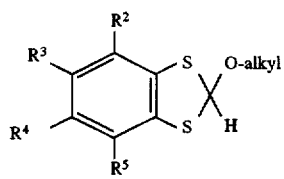
(VIII)

which can be prepared in accordance with literature instructions (J. Nakayama, Synthesis 38 (1975)).

The thiols of the formula (V) and the disulphide compounds of the formulae (VI) and (VII) are generally known and can be prepared in accordance with a variety of literature instructions (see e.g. S. Hunig et. al., Liebigs Ann. Chem., 738, 192 (1979); D. M. Giolando, Synthesis, 451 (1992); I. Degani et. al., Synthesis, 471 (1976); J. C. Marten et. al., J. Am. Chem. Soc., 111, 658 (1989)).

The amines of the general formula (IV) are generally known and can in the majority of cases be obtained commercially.

The active compounds of the formulae (I), (Ia) and (II) have a strong microbicidal action and can be used in practice to combat unwanted microorganisms. The active compounds of the formulae (I), (Ia) and (II) are suitable for protecting industrial materials against infestation and destruction by unwanted microorganisms.

Industrial materials in the present context are to be understood as meaning non-living materials which have been prepared for use in industry. Examples of industrial materials which are to be protected from microbial alteration or destruction by active compounds according to the invention can be adhesives, sizes, paper and board, textiles, leather, wood, coating compositions and plastics articles, cooling lubricants and other materials which can be infested with or destroyed by microorganisms. Within the scope of the materials to be protected mention may also be made of parts of production plants, for example cooling-water circuits, which may be adversely affected by the multiplication of microorganisms. Industrial materials which may preferably be mentioned within the scope of the present invention are adhesives, sizes, papers and boards, leather, wood, coating compositions, cooling lubricants and heat-transfer liquids.

Examples of microorganisms capable of bringing about degradation or alteration of the industrial materials are bacteria, fungi, yeasts, algae and slime organisms. The active compound and/or compositions according to the invention preferably act against fungi, in particular moulds, and against slime organisms and algae.

Microorganisms of the following genera may be mentioned by way of example:
Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds of the formulae (I), (Ia) and (II) can be converted to the customary formulations, such as solutions, emulsions, suspensions, powders, foams, pastes, granules, aerosols and very fine capsules in polymeric substances.

These formulations and compositions are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The activity and the spectrum of action of the active compounds of the formulae (I), (Ia) and (II) and/or of the compositions, precursors or, quite generally, formulations which can be prepared therefrom can be increased if, optionally, further antimicrobially active compounds, fungicides, bactericides, herbicides, insecticides or other active compounds are added in order to enlarge the spectrum of action or to achieve particular effects, for example additional protection against insects. These mixtures may possess a broader spectrum of action than the compounds according to the invention.

In many cases synergistic effects are obtained if this is done; in other words, the activity of the mixture is greater than the activity of the individual components. Examples are particularly favourable co-components of the following compounds:

Triazoles such as:

amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, metconazole, epoxyconazole, paclobutrazol, penconazole, propioconazole, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

Imidazoles such as:

imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

Methyl(E)-2-[2-[6-(2-cyanophenoxy)pyrimidin-4-yloxy]phenyl]-3-methoxyacrylate, methyl(E)-2-[2-[6-(2-thioamidophenoxy)pyrimidin-4-yloxy]phenyl]-3-methoxyacrylate, methyl(E)-2-[2-[6-(2-fluorophenoxy)pyrimidin-4-yloxy]phenyl]-3-methoxyacrylate, methyl(E)-2-[2-[6-(2,6-difluorophenoxy)pyrimidin-4-yloxy]phenyl]-3-methoxyacrylate, methyl(E)-2-[2-[3-(pyrimidin-2-yloxy)phenoxy)phenyl]-3-methoxyacrylate, methyl(E)-2-[2-[3-(5-methylpyrimidin-2-yloxy)-phenoxy]phenyl]-3-methoxyacrylate, methyl(E)-2-[2-[3-(phenyl-sulphonyloxy)phenoxy]phenyl]-3-methoxyacrylate, methyl(E)-2-[2-[3-(4-nitrophenoxy)phenoxy]phenyl]-3-methoxyacrylate, methyl(E)-2-[2-(3,phenoxyphenyl]-3-methoxyacrylate, methyl(E)-2-[2-(3,5-dimethylbenzoyl)pyrrol-1-yl]-3-methoxyacrylate, methyl(E)-2-[2-(3-methoxyphenoxy)phenyl]-3-methoxyacrylate, methyl(E)-2-[2-(2-phenylethen-1-yl)-phenyl]-3-methoxyacrylate, methyl(E)-2-[2-(3,5-dichlorophenoxy)pyridin-3-yl]-3-methoxyacrylate, methyl(E)-2-(2-(3-(1,1,2,2-tetrafluoroethoxy)-phenoxy)phenyl)-3-methoxyacrylate, methyl(E)-2-(2-[3-(alpha-hydroxybenzyl)-phenoxy]phenyl)-3-methoxyacrylate, methyl(E)-2-(2-(4-phenoxypyridin-2-yloxy)-phenyl)-3-methoxyacrylate, methyl(E)-2-[2-(3-n-propyloxyphenoxy)phenyl]-3-methoxyacrylate, methyl (E)-2-[2-(3-isopropyloxyphenoxy)phenyl]-3-methoxyacrylate, methyl(E)-2-[2-[3-(2-fluorophenoxy) pehnoxy]phenyl]-3-methoxyacrylate, methyl(E)-2-[2-(3-ethoxy-phenoxy)phenyl]-3-methoxyacrylate, methyl(E)-2-[2-(4-tert.-butylpyridin-2-yloxy)-phenyl]-3-methoxyacrylate, methyl(E)-2-[2-[3-(3-cyanophenoxy)phenoxy]phenyl]-3-methoxyacrylate, methyl(E)-2-[2-(3-methylpyridin-2-yloxymethyl)phenyl]-3-methoxyacrylate, methyl(E)-2-[2-|6-(2-methylphenoxy)pyrimidin-4-yloxy]phenyl]-3-methoxyacrylate, methyl (E)-2-[2-(5-bromopyridin-2-yloxymethyl)phenyl]-3-methoxyacrylate, methyl(E)-2-[2-(3-(3-iodopyridin-2-yloxy)phenoxy)-phenyl]-3-methoxyacrylate, methyl-(E)-2-[2-[6-(2-chloropyridin-3-yloxy)pyrimidin-4-yloxy]phenyl]-3-methoxyacrylate, (E),(E)methyl-2-[2-(5,6-dimethylpyrazin-2-ylmethyl-oximinomethyl)phenyl]-3-methoxy-acrylate, (E)-methyl-2-{2-[6-(6-methylpyridin-2-yloxy)pyrimidin-4-yloxy|phenyl}-3-methoxyacrylate, (E),(E)methyl-2-{2-(3-methoxyphenyl)methyloximinomethyl]phenyl}-3-methoxyacrylate, (E)methyl-2-{2-(6-(2-azidophenoxy)-pyrimidin-4-yloxy]phenyl}3-methoxyacrylate, (E),(E)methyl-2-{2-[6-phenylpyrimidin-4-yl)-methyloximino-methyl]phenyl}-3-methoxyacrylate, (E),(E)methyl-2-{2-[(4-chlorophenyl)-methylox-iminomethyl]phenyl}-3-methoxyacrylate, (E)methyl-2-{2-|6-(2-n-propylphenoxy)-1,3,5-triazin-4-yloxy|phenyl}-3-methoxyacrylate, (E),(E)methyl-2-{2-[(3-nitrophenyl)methyloximinomethyl]phenyl}-3-methoxyacrylate;

Succinate dehydrogenase inhibitors such as:

fenfuram, furcarbanil, cyclafluramid, furmecyclox, Seedvax, metsulfovax, pyrocarbolid, oxycarboxin, shirlan, mebenil (mepronil), benodanil, flutolanil (Moncut); naphthalene derivatives such as terbinafine, naftifine, butenafine, 3-chloro-7-(2-aza-2,7,7-trimethyloct-3-en-5-ine);

sulphenamides such as dichlofluanid, tolylfluanid, folpet, fluorfolpet; captan, captofol; benzimidazoles, such as carbendazim, benomyl, furathiocarb, fuberidazole, thiophonatmethyl, thiabendazole or salts thereof;

morpholine derivatives, such as tridemorph, fenpropimorph, falimorph, dimethomorph, dodemorph, aldimorph, fenpropidin and their arylsulphonic acid salts, for example p-toluenesulphonic acid and p-dodecylphenyl-sulphonic acid;

dithiocarbamate, cufraneb, ferbam, mancopper, mancozeb, maneb, metam, metiram, thiram zeneb, ziram;

benzothiazoles such as 2-mercaptobenzothiazole;

benzamides, such as 2,6-dichloro-N-(4-trifluoromethylbenzyl)-benzamide;

boron compounds, such as boric acid, boric esters, borax;

formaldehyde and formaldehyde donor compounds, such as benzyl alcohol mono-(poly)-hemiformal, oxazolidines, hexa-hydro-S-triazines, N-methylolchloroacetamide, paraformadehyde, nitropyrin, oxolinic acid, tecloftalam;

tris-N-(cyclohexyldiazeniumdioxy)-aluminium, N-(cyclohexyldiazeniumdioxy)-tributyltin and K salts, bis-N-(cyclohexyldiazeniumdioxy)-copper;

N-methylisothiazolin-3-one, 5-chloro-N-methylisothiazolin-3-one, 4,5-dichloro-N-octylisothiazolin-3-one, N-octyl-isothiazolin-3-one, 4,5-trimethylene-isothiazolinones, 4,5-benzisothiazolinones, N-methylolchloroacetamide;

aldehydes such as cinnamaldehyde, formaldehyde, glutaraldehyde, β-bromocinnamaldehyde;

thiocyanates, such as thiocyanatomethylthiobenzothiazole, methylene bisthiocyanate, etc.;

quaternary ammonium compounds, such as benzyldimethyltetradecylammonium chloride, benzyldimethyldodecylammonium chloride, didecyldimethaylammonium chloride;

iodine derivatives, such as diiodomethyl p-tolyl sulphone, 3-iodo-2-propinyl alcohol, 4-chlorophenyl 3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexylcarbamate, 3-iodo-2-propinyl phenylcarbamate;

phenol derivatives, such as tribromophenol, tetrachlorophenol, 3-methyl-4-chlorophenol, 3,5-dimethyl-4-chlorophenol, phenoxyethanol, dichlorphen, o-phenylphenol, m-phenylphenol, p-phenylphenol, 2-benzyl-4-chlorophenol and their alkali metal and alkaline earth metal salts;

microbicides with an activated halogen group, such as chloroacetamide, bronopol, bronidox, tectamers such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;

pyridines, such as 1-hydroxy-2-pyridinethione (and its Na, Fe, Mn and Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;

metal soaps, such as tin, copper, zinc naphthenate, octoate, 2-ethylhexanoate, oleate, phosphate, benzoate;

metal salts, such as copper hydroxycarbonate, sodium dichromate, potassium dichromate, potassium chromate, copper sulphate, copper chloride, copper borate, zinc fluorosilicate, copper fluorosilicate;

oxides, such as tributyltin oxide, $Cu_2O$, CuO, ZnO;

dialkyldithiocarbamates, such as Na salts and Zn salts of dialkyldithiocarbamates, tetramethylthiuram disulphide, potassium N-methyl-dithiocarbamate;

nitriles such as 2,4,5,6-tetrachloroisophthalodinitrile, disodium cyanodithioimidocarbamate;

quinolines, such as 8-hydroxyquinoline and Cu salts thereof;

mucochloric acid, 5-hydroxy-2(5H)-furanone;

4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine 2-thione, N-(2-p-chlorobenzoylethyl)-hexaminium chloride, potassium N-hydroxymethyl-N'-methyl-dithiocarbamate, 2-oxo-2-(4-hydroxy-phenyl) acethydroximic acid chloride, phenyl 2-chloro-cyano-vinyl sulphone, phenyl 1,2-dichloro-2-cyano-vinyl sulphone;

Ag, Zn or Cu-containing zeolites alone or enclosed in polymeric active compounds.

Very particular preference is given to mixtures with azaconazole, bromuconazole, cyproconazole, dichlobutrazol, diniconazole, hexaconazole, metaconazole, penconazole, propiconazole, tebuconazole, methyl (E)-methoximino[α-(o-tolyloxy)-o-tolyl)]acetate, methyl (E)-2-{2-[6-(2-cyanophenoxy)-pyrimidin-4-yl-oxy]phenyl}-3-methoxyacrylate, methfuroxam, carboxin, fenpiclonil, 4-(2,2-difluoro-1,3-benzodioxol-4-yl)-1H-pyrrol-3-carbonitrile, butenafine, imazalil, N-methyl-isothiazolin-3-one, 5-chloro-N-methylisothiazolin-3-one, N-octylisothiazolin-3-one, benzisothiazolinones, N-(2-hydroxypropyl)-aminomethanol, benzyl alcohol (hemi)-formal, glutaraldehyde, omadine, dimethyl dicarbonate, and/or 3-iodo-2-propinyl n-butylcarbamates.

Furthermore, highly effective mixtures are also prepared with the following active compounds:

Fungicides:
acypetacs, 2-aminobutane, ampropylfos, anilazine, benalaxyl, bupirimate, chinomethionat, chloroneb, chlozolinate, cymoxanil, dazomet, diclomezine, dichloram, diethofencarb, dimethirimol, diocab, dithianon, dodine, drazoxolon, edifenphos, ethirimol, etridiazole, fenarimol, fenitropan, fentin acetate, fentin hydroxide, ferimzone, fluazinam, fluromide, flusulfamide, flutriafol, fosetyl, fthalide, furalaxyl, guazatine, hymexazol, iprobenfos, iprodione, isoprothiolane, metalaxyl, methasulfocarb, nitrothalisopropyl, nuarimol, ofurace, oxadiyl, perflurazoate, pencycuron, phosdiphen, pimaricin, piperalin, procymidone, propamocarb, propineb, pyrazophos, pyrifenox, pyroquilon, quintozene, tar oils, tecnazene, thicyofen, thiophanate-methyl, tolclofos-methyl, triazoxide, trichlamide, tricyclazole, triforine, vinclozolin.

Insecticides:
phosphoric esters, such as azinphos-ethyl, azinphos-methyl, α-1(4-chlorophenyl)-4-O-ethyl, S-propyl) phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulfprofos, triazophos and trichlorphon;

carbamates, such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds, preferably dimethyl(phenyl)silylmethyl 3-phenoxybenzyl ethers, such as dimethyl-(4-ethoxyphenyl)-silylmethyl 3-phenoxybenzyl ether, or (dimethylphenyl)-silyl-methyl 2-phenoxy-6-pyridylmethyl ethers, such as, for example, dimethyl-(9-ethoxy-phenyl)-silylmethyl 2-phenoxy-6-pyridylmethyl ether, or [(phenyl)-3-(3-phenoxyphenyl)-propyl] (dimethyl)-silanes, for example (4-ethoxyphenyl)-[3-(4-fluoro-3-phenoxyphenyl-propyl]dimethyl-silane, silafluofen;

pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropanecarboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]-4,5-dihydro-N-nitro-1H-imidazol-2amine(imidacloprid), N-[(6-chloro-3-pyridyl)methyl-] $N^2$-cyano-$N^1$-methylacetamide (NI-25);

abamectin, AC 303, 630, acephate, acrinathrin, alanycarb, aldoxycarb, aldrin, amitraz, azamethiphos, Bacillus thuringiensis, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulphuryl fluoride, tar oils, teflubenzuron, tefluthrin, temephos, terbufos, tetrachlorvinphos, tetramethrin, O-2-tert-butyl-pyrimidin-5-yl-o-isopropyl-phosphorothiate, thiocyclam, thiofanox, thiometon, tralomethrin, trifluomuron, trimethacarb, vamidothion, Verticillium lacanii, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, chinomethionate, chlordane, chlorfenvinphos, chlorfluazuron, chlormephos, chloropicrin, chlorpyrifos, cyanophos, beta-cyfluthrin, alpha-cypermethrin, cyophenothrin, cyromazine, dazomet, DDT, demeton-S-methylsulphon, diafenthiuron, dialifos, dicrotophos, diflubenzuron, dinoseb, deoxabenzofos, diaxacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous, chloride, metam, Metarthizium, anisopliae, methacrifos, methamidophos, methidathion, methiocarb, methoprene, methoxychlor, methyl isothiocyanate, metolcarb, mevinphos, monocrotophos, naled, Neodiprion sertifer NPV, nicotine, omethoate, oxydemeton-methyl, pentachlorophenol, petroleum oils, phenothrin, phenthoate, phorate;

Molluscicides:
Fentin acetate, metaldehyde, methiocarb, niclosamide, thiodicarb, trimethacarb.

Algicides:
Copper sulphate, dichlororphen, endothal, fentin acetate, quinoclamine.

Heibicides: acetochlor, acifluorfen, aclonifen, acrolein, alachlor, alloxydim, ametryn, amidosulfuron, amitrole, ammonium sulfamate, anilofos, asulam atrazine, aziptrotryne, benazolin, benfluralin, benfuresate, bensulfuron, bensulfide, bentazone, benzofencap, benzthiazuron, bifenox, bilanafos, borax, dichlorprop, dichlorprop-P, diclofop, diethatyl, difenoxuron, difenzoquat, diflufenican, dimefuron, dimepiperate, dimethachlor, dimethametryn, dimethipin, dimethylarsinic acid, dinitramine, dinoseb, dinoseb, dinoseb acetate, dinoseb, bromacil, bromobutide, bromofenoxim, bromoxynil, butachlor, butamifos, fuenachlor, butralin, butylate, carbetamide, CGA 184927, chlormethoxyfen, chloramben, chlorbromuron, chlorbutam, chlorfurenol, chloridazon, chlorimuron, chlornitrofen, chloroacetic acid, achloropicrin, chlorotoluron, chloroxuron, chlorpropham, chlorsulfuron, chlorthal, chlorthiamid, cirnethylin, cinofulsuron, clethodim, clomazone, clomeprop, clopyralid, cyanamide, cyanazine, dinoseb acetate, dinoterb, diphenamid, dipropetryn, diquat, dithiopyr, diduron, DNOC, PPX-A 788, DPX-E96361, DSMA, eglinazine, endothal, EPTC, esprocarb, ethalfluralin, ethidimuron, ethofumesate, fenoxaprop, fenoxaprop-P, fenuron, flamprop, flamprop-M, flazasulfuron, fluazifop, fluazifop-P, fluchloralin, flumeturon, fluorocgycofen, fluoronitrofen, flupropanate, flurenol, fluridone, flurochloridone, fluoroxypyr, cycloate, cycloxydim, 2,4-D, daimuron, dalapon, dazomet, 2,4-DB, desmedipham, desmetryn, dicamba, dichlorbenil, isoproturon, isouron, isoxaben, isoxapyrifop, lactofen, lenacil, linuron, LS830556, MCPA, MCPA-thioethyl, MCPB, mecoprop, mecoprop-P, mefenacet, mefluidide, metam, metamitron, metazachlor, methabenzthiazuron, methazole, methoproptryne, methyldymron, methylisothiocyanate, metobromuron, fomosafen, fosamine, furyloxyfen, glufosinate, glyphosate, haloxyfop, hexazinone, imazamethabenz, imazapyr, imazaquin, imazethapyr, ioxynil, isopropalin, propyzamide, prosulfocab, pyrazolynate, pyrazolsulfuron, pyrazoxyfen, pyributicarb, pyridate, quinclorac, quinmerac, quinocloamine, quizalofop, quzizalofop-P, S-23121, sethoxydim, sifuron, simazine, simetryn, SMY 1500, sodium chlorate, sulfometuron, tar oils, TCA, metolachlor, metoxuron, metribzin, metsulfuron, molinate, monalide, monolinuron, MSMA, naproanilide, napropamide, naptalam, neburon, nicosulfuron, nipyraclofen, norflurazon, orbencarb, oaryzalin, oxadiazon, oxyfluorfen, paraquat, pebulate, pendimethalin, pentachlorophenol, pentaochlor, petroleum oils, phenmedipham, picloram, piperophos, pretilachlor, primisulfuron, prodiamine, proglinazine, propmeton, prometryn, propachlor, tebutam, tebuthiuron, terbacil, terbumeton, terbuthylazine, terbutryn, thiazafluoron, thifensulfuron, thiobencarb, thiocarbazil, tioclorim, tralkoxydim, tri-allate, triasulfuron, tribenzuron, triclopyr, tridiphane, trietazine, trifluralin, IBI-C4874 vernolate, propanil, propaquizafop, propazine, propham.

The weight ratios of the active compounds in these active-compound combinations can be varied within relatively large ranges.

The active-compound combinations preferably receive the active compound in a proportion of from 0.1 to 99.9%, in particular from 1 to 75%, particularly preferably from 5 to 50%, the remainder to 100% being made up by one or more of the abovementioned co-components.

The microbicidal compositions or concentrates used to protect the industrial materials contain the active compound and/or the active-compound combination in a concentration of from 0.01 and 95% by weight, in particular from 0.1 to 60% by weight.

The concentrations in which the active compounds and/or active-compound combinations which are to be used are employed depends on the nature and the incidence of the microorganisms to be combated and on the composition of the material to be protected. The optimum quantity for use can be determined by series of tests. The concentrations for use are in general in the range from 0.001 to 5% by weight, preferably from 0.05 to 1.0% by weight, based on the material to be protected.

The active compounds and compositions according to the invention make it possible in an advantageous manner to replace the microbicidal compositions which have been available to date by more effective compositions. They exhibit good stability and, advantageously, have a broad spectrum of action.

The examples which follow serve to illustrate the invention. The invention is not limited to the examples.

PREPARATION EXAMPLES

Example 1

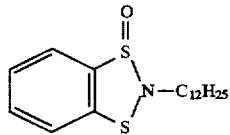

1.35 g (4.2 mmol) of N-(n-dodecyl)-benzodithiazole are dissolved in 20 ml of chloroform, the solution is cooled to −20° C., and a total of 1.26 g (4 mmol) of 56% strength m-chloroperbenzoic acid are added in portions. The mixture is subsequently stirred at 0° C. for 2 h, washed with saturated NaHCO$_3$ solution and saturated NaCl solution, dried over Na$_2$SO$_4$ and concentrated.

The residue is purified by chromatography on silica gel (toluene:ethyl acetate=1:1).

Yield: 0.7 g (Δ 50% of theory) of a pale yellow oil; $^1$H-NMR(CDCl$_3$)δ=0.9(3H, t); 1.1–1.7(23H, m); 3.5(2H, t); 7.2–7.9(4H, m).

In analogy to this example and in accordance with the general instructions above, the compounds of the formula (I) which are listed in Table 1 below are also prepared.

TABLE 1

(I)

| Ex. No. | R$^1$ | R$^2$ | R$^3$ | R$^4$ | R$^5$ | Physical constants |
|---|---|---|---|---|---|---|
| 1 | —C$_{12}$—H$_{25}$ | H | H | H | H | see Preparation Example |
| 2 | —C$_8$H$_{17}$ | H | H | H | H | $^1$H-NMR (CDCl$_3$) δ=0.85 (3H, t), 1.2–1.5 (10H, m), 1.85 (2H, tq), 3.50 (2H, t), 7.30 (1H, m), 7.48 (2H, m), 7.85 (1H, d). |
| 3 | —H | H | H | H | H | |
| 4 | —CH$_3$ | H | H | H | H | $^1$H-NMR (CDCl$_3$) δ=3.25 (3H, s); 7.3 (1H, m); 7.5 (2H, m); 7.83 (1H, d). |
| 5 | —C$_2$H$_5$ | H | H | H | H | $^1$H-NMR (CDCl$_3$) δ=1.43 (3H, t); 3.57 (2H, q); 7.26 (1H, m); 7.49 (2H, m); 7.81 (1H, d). |
| 6 | —C$_3$H$_7$ | H | H | H | H | $^1$H-NMR (CDCl$_3$) δ=1.0 (3H, t); 1.82 (2H, m); 3.47 (2H, t); 7.29 (1H, m); 7.4 (2H, m); 7.83 (1H, d). |
| 7 | —CH(CH$_3$)$_2$ | H | H | H | H | $^1$H-NMR (CDCl$_3$) δ=1.38 (3H, d); 1.44 (3H, d); 4.12 (1H, m); 7.3 (1H, m); 7.46 (2H, m); 7.8 (1H, d). |
| 8 | —C$_4$H$_9$ | H | H | H | H | $^1$H-NMR (CDCl$_3$) δ=0.95 (3H, t); 1.45 (2H, m); 1.75 (2H, m); 3.50 (2H, t); 7.30 (1H, m); 7.45 (2H, m); 7.80 (1H, d). |
| 9 | —CH$_2$CH(CH$_3$)$_2$ | H | H | H | H | $^1$H-NMR (CDCl$_3$) δ=1.0 (6H, m); 2.1 (1H, m); 3.27 (2H, d); 7.26 (1H, m); 7.45 (2H, m); 7.82 (1H, d). |
| 10 | —CH(CH$_3$)(C$_2$H$_5$) | H | H | H | H | $^1$H-NMR (CDCl$_3$) δ=0.88/0.99 (3H, 2×d); 1.26/1.43 (3H, 2×t); 1.5–1.9 (2H, m); 3.9 (1H, m); 7.3 (1H, m); 7.48 (2H, m); 7.82 (1H, d). (Diastereomer mixture) |
| 11 | —CH$_2$CH=CH$_2$ | H | H | H | H | $^1$H-NMR (CDCl$_3$) δ=4.1 (2H, d); 5.3–5.5 (2H, m); 6.0 (1H, m); 7.30 (1H, m); 7.45 (2H, m); 7.80 (1H, d). |
| 12 | —CH$_2$≡CH | H | H | H | H | $^1$H-NMR (CDCl$_3$) δ=2.37 (2H, m); 4.29 (2H, AB system); 7.3 (1H, m); 7.45 (2H, m); 7.8 (1H, d). |
| 13 | —C$_5$H$_{11}$ | H | H | H | H | $^1$H-NMR (CDCl$_3$) δ=0.9 (3H, t); 1.3 (4H, m); 1.78 (2H, m); 3.49 (2H, t); 7.3 (1H, m); 7.45 (2H, m); 7.80 (1H, d). |
| 14 | —C$_6$H$_{13}$ | H | H | H | H | $^1$H-NMR (CDCl$_3$) δ=0.9 (3H, t); 1.3 (6H, m); 3.50 (2H, t); 7.32 (1H, m); 7.45 (2H, m); 7.80 (1H, d). |
| 15 | —C$_7$H$_{15}$ | H | H | H | H | $^1$H-NMR (CDCl$_3$) δ=0.9 (3H, t); 1.35 (8H, m); 3.50 (2H, t); 7.30 (1H, m); 7.45 |

TABLE 1-continued

(I)

| Ex. No. | R¹ | R² | R³ | R⁴ | R⁵ | Physical constants |
|---|---|---|---|---|---|---|
| | | | | | | (2H, m); 7.80 (1H, d). |
| 16 | —C₉C₁₉ | H | H | H | H | |
| 17 | —C₁₀H₂₁ | H | H | H | H | |
| 18 | —C₁₁H₂₃ | H | H | H | H | |
| 19 | —C₁₃H₂₇ | H | H | H | H | |
| 20 | —CH₂CH₂OCH₃ | H | H | H | H | ¹H-NMR (CDCl₃) δ=3.25 (3H, s); 3.5–3.8 (4H, m); 7.27 (1H, m); 7.48 (2H, m); 7.80 (1H, d). |
| 21 | 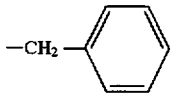 | H | H | H | H | ¹H-NMR (CDCl₃) δ=1.5–2.2 (8H, m); 4.07 (1H, m); 7.30 (1H, m); 7.48 (2H, m); 7.80 (1H, d). |
| 22 |  —CH₂— | H | H | H | H | ¹H-NMR (CDCl₃) δ=4.63 (2H, AB system); 7.2–7.4 (8H, m); 7.80 (1H, d). |
| 23 | 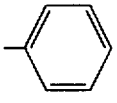 | H | H | H | H | ¹H-NMR (CDCl₃) δ=0.9–1.1 (4H, m); 2.93 (1H, m); 7.3 (1H, m); 7.48 (2H, m); 7.80 (1H, d). |
| 24 | 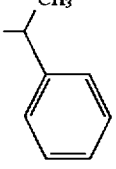 | H | H | H | H | ¹H-NMR (CDCl₃) δ=7.1–7.6 (8H, m); 7.88 (1H, d). |
| 25 | 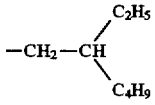 CH₃ | H | H | H | H | ¹H-NMR (CDCl₃) δ=1.85 (3H, t); 4.90/4.90 (1H, 2× q); 7.1–7.5 (8H, m); 7.82 (1H, d). |
| 26 | —CH₂—CH(C₂H₅)(C₄H₉) | H | H | H | H | ¹H-NMR (CDCl₃) δ=0.8–1.0 (6H, m); 1.2–1.6 (8H, m); 1.79 (1H, m); 3.39 (2H, m); 7.3 (1H, m); 7.48 (2H, m); 7.82 (1H, d). |
| 27 | —C₁₆H₃₃ | H | H | H | H | ¹H-NMR (CDCl₃) δ=0.87 (3H, t); 1.2 (26H, m); 1.81 (2H, m); 3.50 (2H, t); 7.3 (1H, m); 7.48 (2H, m); 7.82 (1H, d). |
| 28 | —C₁₈H₃₇ | H | H | H | H | ¹H-NMR (CDCl₃) δ=0.87 (3H, t); 1.2 (28H, m); 1.80 (2H, m); 3.48 (2H, t); 7.3 (1H, m); 7.48 (2H, m); 7.80 (1H, d). |
| 29 | —(CH₂)₄— 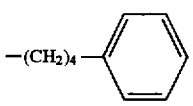 | H | H | H | H | ¹H-NMR (CDCl₃) δ=2.6–2.9 (4H, m); 2.67 (2H, t); 3.50 (2H, t); 7.1–7.5 (8H, m); 7.82 (1H, d). |
| 30 | —C₁₄H₂₉ | H | H | H | H | ¹H-NMR (CDCl₃) δ=0.87 (3H, t); 1.2 (24H, m); 1.81 (2H, m); 3.49 (2H, t); 7.30 (1H, m); 7.50 (2H, m); 7.82 |

TABLE 1-continued (Structure I: benzene ring with R⁵, R⁴, R³, R² substituents fused to a 5-membered ring containing S, N—R¹, and SO) (I)

| Ex. No. | R¹ | R² | R³ | R⁴ | R⁵ | Physical constants |
|---|---|---|---|---|---|---|
| | | | | | | (1H, d). |
| 31 | —(CH₂)₃OC₄H₉ | H | H | H | H | ¹H-NMR (CDCl₃) δ=0.92 (3H, t); 1.35 (2H, m); 1.55 (2H, m); 2.07 (2H, m); 3.44 (2H, t); 3.49 (2H, t); 3.65 (2H, t); 7.31 (1H, m); 7.50 (2H, m); 7.81 (1H, d). |
| 32 | —CH₂-(furan) | H | H | H | H | ¹H-NMR (CDCl₃) δ=4.6 (2H, AB system); 6.35 (1H, d); 6.46 (1H, d); 7.25–7.55 (4H, m); 7.83 (1H, d). |
| 33 | —C₈C₁₇ | H | H | F | H | ¹H-NMR (CDCl₃) δ=0.8 (3H, t); 1.2 (10H, m); 0.8–2.0 (2H, m); 3.5/3.9 (2H, 2×t); 7.0–8.0 (3H, m). |
| 34 | —(CH₂)₂O-phenyl | H | H | H | H | ¹H-NMR (CDCl₃) δ=3.97 (2H, m); 4.23 (2H, m); 6.9–7.5 (8H, m); 7.84 (1H, d). |
| 35 | —cyclohexyl | H | H | H | H | ¹H-NMR (CDCl₃) δ=1.0–2.2 (10H, m); 3.7 (1H, m); 7.3 (1H, m); 7.48 (2H, m); 7.84 (1H, d). |
| 36 | —C(CH₃)₄ | H | H | H | H | ¹H-NMR (CDCl₃) δ=1.61 (9H, s); 7.26 (1H, m); 7.48 (2H, m); 7.80 (1H, d). |
| 37 | —CH(CH₃)(C₃H₇) | H | H | H | H | oil |
| 38 | —CH(CH₂CH₂OCH₃)(CH₃) | H | H | H | H | ¹H-NMR (CDCl₃) δ=1.1–1.2 (6H, m); 1.48 (2H, d); 1.7–2.0 (2H, m); 3.3–3.7 (4H, m); 4.2–4.4 (1H, m); 7.3 (1H, m); 7.48 (2H, m); 7.81 (1H, d). |
| 39 | —cyclohexyl-OEt | H | H | H | H | ¹H-NMR (CDCl₃) δ=1.23 (3H, t); 1.3–2.3 (8H, m); 3.2 (1H, m); 3.5 (2H, q); 3.7 (1H, m); 7.3 (1H, m); 7.45 (2H, m); 7.81 (1H, d). |
| 40 | —cycloC₆H₁₅ | H | H | H | H | ¹H-NMR (CDCl₃) δ=1.3–2.1 (14H, m); 4.05 (1H, m); 7.35 (1H, m); 7.45 (2H, m); 7.85 (1H, d). |
| 41 | —CH₂CH(OC₂H₅)₂ | H | H | H | H | ¹H-NMR (CDCl₃) δ=1.3 (6H, m); 3.4–3.8 (6H, m); 4.74 (1H, m); 7.26 (1H, m); 7.48 (2H, m); 7.84 (1H, m). |
| 42 | —CH₃ | H | Cl | H | Cl | ¹H-NMR (CDCl₃) δ=3.26 (3H, s); 7.45 (1H, s); 7.71 (1H, s). |
| 43 | —CH₂CH=CH₂ | H | Cl | H | Cl | ¹H-NMR (CDCl₃) δ=4.1 (2H, m); 5.5 (2H, m); 5.98 |

TABLE 1-continued

![Formula I structure with R2, R3, R4, R5 substituents on benzene ring fused to N-R1, S, SO heterocycle]  (I)

| Ex. No. | R¹ | R² | R³ | R⁴ | R⁵ | Physical constants |
|---|---|---|---|---|---|---|
| | | | | | | (1H, m); 7.25/7.34/7.46/ 7.71 (2H, 4xs). |
| 44 | —C₈H₁₇ | H | Cl | H | Cl | ¹H-NMR (CDCl₃) δ=0.88 (3H, t); 1.3 (9H, m); 1.90 (2H, m); 3.84 (2H, t); 7.6–7.9 (2H, 4xs). |
| 45 | —(CH₂CH₂O)₃OC₂H₅ | H | H | H | H | ¹H-NMR (CDCl₃) δ=1.21 (3H, t); 3.45–3.9 (14H, m); 7.35 (1H, m); 7.48 (2H, m); 7.82 (1H, d). |
| 46 | —CH₂CH₂OH | H | H | H | H | ¹H-NMR (CDCl₃) δ=2.95 (1H, br), 3.6–4.0 (4H, m); 7.35 (1H, m); 7.52 (2H, m); 7.85 (1H, d). |
| 47 | —CH₂CO₂Et | H | H | H | H | ¹H-NMR (CDCl₃) δ=1.19 (t, 3H); 4.16 (q, 2H); 4.26 (d, 2H); 7.32–7.51 (m, 3H); 7.85 (m, 1H). |
| 48 | CH(Ph)CO₂ᵗBu | H | H | H | H | ¹H-NMR (CDCl₃) δ=1.38 and 1.43 (s, 9H); 2.16 (s, 1H); 7.26–7.52 (m, 8H); 7.75 (m, 1H). |
| 49 | —CH(CH₃)CO₂CH₃ | H | H | H | H | ¹H-NMR (CDCl₃) δ=1.65 (3H); 3.49 and 3.69 (3H); 4.49–4.71 (1H); 7.27–7.49 (3H); 7.83 (1H). |
| 50 | —CH(CH₂CH(CH₃)₂)CO₂CH₃ | H | H | H | H | ¹H-NMR (CDCl₃) δ=3.45 and 3.68 (3H); 4,52 (1H); 7.30–7.48 (3H); 7.86 (1H). |
| 51 | CH(i-Pr)CO₂Et | H | H | H | H | ¹H-NMR (CDCl₃) δ=0.87– 1.26 (9H); 2.43 (1H); 3.88 (1H); 4.03–4.20 (2H); 7.21–7.34 (m, 1H); 7.47 (1H); 7.82 (1H). |
| 52 | —CH(CH₂Ph)CO₂Et | H | H | H | H | MS: m/z 348 |

Example II-1

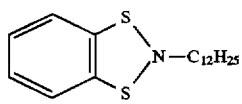

2.11 g (10 mmol) are dissolved in ether and the solution is added dropwise to a mixture, cooled at −20° C., of 1.85 g (10 mol) of dodecylamine and 2.42 g (24 mmol) of triethylamine. The mixture is stirred at room temperature for 5 h and filtered and the filtrate is concentrate on a rotary evaporator. Purification by chromatography on silica gel (toluene).

Yield: 2.5 g (Δ 74% of theory); ¹H-NMR(CDCl₃)δ=0.85 (3H, t), 1.1–1.3(21H, m), 1.5(2H, m), 2.85(2H, t), 7.1–7.5 (4H, m).

In analogy to this example and in accordance with the general instructions above, the compounds of the formula (II) which are listed in Table 2 below are also prepared.

TABLE 2

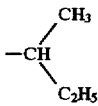

| Ex. No. | $R^1$ | $R^2$ | $R^3$ | $R^4$ | $R^5$ | Physical constants |
|---|---|---|---|---|---|---|
| 1 | $-C_{12}-H_{25}$ | H | H | H | H | see Preparation Example II-1 |
| 2 | $-C_8H_{17}$ | H | H | H | H | $^1$H-NMR(CDCl$_3$) δ=0.85 (3H, t), 1.1–1.4 (10H, m), 1.55 (2H, m), 2.90 (2H, t), 7.15 (2H, m), 7.35 (2H, m) |
| 3 | $-H$ | H | H | H | H | |
| 4 | $-CH_3$ | H | H | H | H | $^1$H-NMR (CDCl$_3$), δ=2.9 (3H, s); 7.15 (2H, m); 7.35 (2H, m). |
| 5 | $-C_2H_5$ | H | H | H | H | $^1$H-NMR(CDCl$_3$), δ= 1.05 (3H, t); 2.95 (2H, q); 7.20 (2H, m); 7.35 (2H, m). |
| 6 | $-C_3H_7$ | H | H | H | H | $^1$H-NMR(CDCl$_3$), δ= 0.90 (3H, t); 1.55 (2H, m); 2.85 (2H, t); 7.15 (2H, m); 7.35 (2H, m). |
| 7 | $-CH(CH_3)_2$ | H | H | H | H | $^1$H-NMR (CDCl$_3$), δ= 1.05 (6H, d); 3.0 (1H, dq); 7.10 (2H, m); 7.30 (2H, m). |
| 8 | $-C_4H_9$ | H | H | H | H | $^1$H-NMR(CDCl$_3$), δ= 0.85 (3H, t); 1.30 (2H, m); 1.55 (2H, m); 2.90 (2H, t); 7.15 (2H, m); 7.35 (2H, m). |
| 9 | $-CH_2CH(CH_3)_2$ | H | H | H | H | $^1$H-NMR (CDCl$_3$), δ= 0.90 (6H, d); 1.90 (1H, m); 2.70 (2H, d); 7.15 (2H, m); 7.35 (2H, m). |
| 10 | $-CH\begin{smallmatrix}CH_3\\C_2H_5\end{smallmatrix}$ | H | H | H | H | $^1$H-NMR(CDCl$_3$), δ= 0.85 (3H, t); 1.0 (3H, d); 1.35 (1H, m); 1.60 (1H, m); 2.75 (1H, m); 7.10 (2H, m); 7.35 (2H, m). |
| 11 | $-CH_2CH=CH_2$ | H | H | H | H | $^1$H-NMR (CDCl$_3$), δ= 3.50 (2H, d); 5.1–5.3 (2H, m); 5.8 (1H, m); 7.18 (2H, m); 7.35 (2H, m). |
| 12 | $-CH_2C\equiv CH$ | H | H | H | H | $^1$H-NMR (CDCl$_3$), δ= 2.30 (1H, t); 3.65 (2H, d); 7.15 (2H, m); 7.30 (2H, m). |
| 13 | $-C_5H_{11}$ | H | H | H | H | $^1$H-NMR (CDCl$_3$), δ= 0.85 (3H, t); 1.2 (4H, m); 1.5 (2H, m); 2.85 (2H, t); 7.15 (2H, m); 7.30 (2H, m). |
| 14 | $-C_6H_{13}$ | H | H | H | H | $^1$H-NMR (CDCl$_3$), δ= 0.85 (3H, t); 1.2 (6H, m); 1.50 (2H, m); 2.90 (2H, t); 7.15 (2H, m); 7.35 (2H, m). |
| 15 | $-C_{12}H_{25}$ | H | H | H | H | $^1$H-NMR (CDCl$_3$), δ= 0.90 (3H, t); 1.1–1.7 (20H, m); 2.88 (2H, t); 7.15 (2H, m); 7.35 (2H, m). |

TABLE 2-continued

(II)

| Ex. No. | R¹ | R² | R³ | R⁴ | R⁵ | Physical constants |
|---|---|---|---|---|---|---|
| 16 | 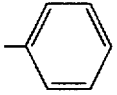 | H | H | H | H | ¹H-NMR (CDCl₃), δ= 0.6–0.8 (4H, m); 2.90 (1H, m); 7.20 (2H, m); 7.38 (2H, m). |
| 17 | 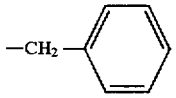 | H | H | H | H | ¹H-NMR (CDCl₃), δ= 7.0–7.5 (9H, m). |
| 18 | —C₇H₁₅ | H | H | H | H | ¹H-NMR (CDCl₃), δ= 0.90 (3H, t); 1.2 (8H, m); 1.50 (2H, m); 2.85 (2H, t); 7.15 (2H, m); 7.35 (2H, m). |
| 19 | —CH₂— 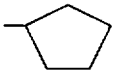 | H | H | H | H | ¹H-NMR (CDCl₃), δ= 4.0 (2H, s); 7.1–7.4 (9H, m). |
| 20 |  | H | H | H | H | ¹H-NMR (CDCl₃), δ= 1.4–1.8 (8H, m); 3.30 (1H, m); 7.15 (2H, m); 7.35 (2H, m). |
| 21 | —(CH₂)₂OCH₃ | H | H | H | H | ¹H-NMR (CDCl₃), δ=3.0 (2H, t); 3.30 (3H, s); 3.5 (2H, t); 7.2 (2H, m); 7.45 (2H, m). |
| 22 | CH₃\\Ph (CH(CH₃)Ph) | H | H | H | H | ¹H-NMR (CDCl₃), δ= 1.45 (3H, d); 3.90 (1H, q); 7.10 (2H, m); 7.2–7.4 (7H, m). |
| 23 | CH(C₄H₉)(C₂H₅) | H | H | H | H | ¹H-NMR (CDCl₃), δ= 0.7–0.9 (6H, m); 1.1–1.7 (8H, m); 2.90 (2H, d); 7.15 (2H, m); 7.35 (2H, m). |
| 24 | —C₁₆H₃₃ | H | H | H | H | ¹H-NMR (CDCl₃), δ= 0.90 (3H, t); 1.2 (26H, m); 1.5 (2H, m); 2.85 (2H, t); 7.20 (2H, m); 7.30 (2H, m). |
| 25 | —C₁₈H₃₇ | H | H | H | H | ¹H-NMR (CDCl₃), δ= 0.90 (3H, t); 0.2 (28H, m); 2.85 (2H, t); 7.15 (2H, m); 7.35 (2H, m). |
| 26 | —(CH₂)₄—  | H | H | H | H | ¹H-NMR (CDCl₃), δ= 1.5 (4H, m); 2.5 (2H, t); 2.9 (2H, t); 7.1–7.4 (9H, m). |
| 27 | —(CH₂)₃—N 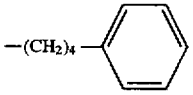 O | H | H | H | H | ¹H-NMR (CDCl₃), δ= 1.75 (2H); 2.40 (6H); 2.95 (2H, t); 3.70 (4H, m); 7.15 (2H, m); 7.35 (2H, m). |
| 28 | —C₁₄H₂₉ | H | H | H | H | ¹H-NMR (CDCl₃), δ= 0.85 (3H, t); 1.25 (22H, m); 1.5 (2H, m); 2.90 |

TABLE 2-continued

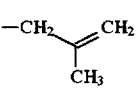 (II)

| Ex. No. | R¹ | R² | R³ | R⁴ | R⁵ | Physical constants |
|---|---|---|---|---|---|---|
| | | | | | | (2H, t); 7.15 (2H, m); 7.35 (2H, m). |
| 29 | —(CH₂)₃—OC₄H₉ | H | H | H | H | ¹H-NMR (CDCl₃), δ=0.8 (3H, t); 1.2 (2H, m); 1.5 (2H, m); 1.8 (2H, m); 3.0 (2H, t); 3.4 (4H, m); 7.1 (2H, m); 7.35 (2H, m). |
| 30 |  | H | H | H | H | ¹H-NMR (CDCl₃), δ= 1.7 (3H, s); 3.4 (2H, s); 4.85 (1H, s); 4.90 (1H, s); 7.15 (2H, m); 7.35 (2H, m). |
| 31 | 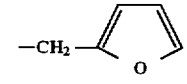 | H | H | H | H | m.p.=158° C. |
| 32 | —C₈H₁₇ | H | H | F | H | ¹H-NMR (CDCl₃), δ=0.8 (3H, t); 1.2 (10H, m); 1.5 (2H, m); 2.9 (2H, t); 6.85 (1H, m); 7.05 (1H, m); 7.20 (1H, m). |
| 33 | 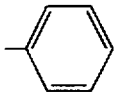 | H | H | H | H | ¹H-NMR (CDCl₃), δ= 3.95 (2H, s); 6.35 (2H, m); 7.2 (2H, m); 7.3 (3H, m). |
| 34 | —(CH₂)₂O— 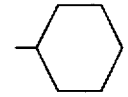 | H | H | F | H | ¹H-NMR (CDCl₃), δ=2.8 (3H, s); 6.9 (1H, dt); 7.1 (1H, dd); 7.25 (1H, m). |
| 35 | 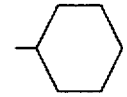 | H | H | H | H | ¹H-NMR (CDCl₃), δ=3.2 (2H, t); 4.0 (2H, t); 7.0– 7.5 (9H, m). |
| 36 |  | H | H | H | H | ¹H-NMR (CDCl₃), δ= 1.0–2.0 (10H, m); 2.50 (1H, m); 7.2 (2H, m); 7.35 (2H, m). |
| 37 | —CH₂CH₂OH | H | H | H | H | ¹H-NMR (CDCl₃), δ=2.0 (1H, br); 3.05 (2H, t); 3.70 (2H, t); 7.15 (2H, br); 7.35 (2H, br). |
| 38 | —CH₂CH—CH₃<br>       \|<br>      OH | H | H | H | H | ¹H-NMR (CDCl₃), δ= 1.05 (3H, d); 2.50 (1H, br); 2.70 (1H, m); 3.05 (1H, m); 3.95 (1H, m); 7.15 (2H, m); 7.35 (2H, m). |
| 39 | —C(CH₃)₄ | H | H | H | H | ¹H-NMR (CDCl₃), δ= 1.05 (9H, s); 7.05 (2H, m); 7.15 (2H, m). |
| 40 |     C₃H₇<br>    \|<br>—CH<br>    \|<br>    CH₃ | H | H | H | H | ¹H-NMR (CDCl₃), δ= 0.80 (3H, t); 1.0 (3H, d); 1.20 (2H, m); 1.50 (2H, m); 2.80 (1H, m). |

TABLE 2-continued

Structure (II): benzo-dithiazole with substituents R², R³, R⁴, R⁵ on the benzene ring and N–R¹

| Ex. No. | R¹ | R² | R³ | R⁴ | R⁵ | Physical constants |
|---|---|---|---|---|---|---|
| 41 | —(CH₂)₃—N(imidazole) | H | H | H | H | $^1$H-NMR (CDCl₃), δ= 2.05 (2H, m); 2.85 (2H, t); 4.30 (2H, t); 7.15 (2H, m); 7.35 (2H, m); 7.95 (1H, s); 8.10 (1H, s). |
| 42 | —CH(C₂H₅)(CH₂CH(C₂H₅)(CH₃)) | H | H | H | H | $^1$H-NMR (CDCl₃), δ= 0.7–0.8 (9H, m); 7.15 (2H, m); 7.35 (2H, m). |
| 43 | —CH(CH₃)(CH₂CH₂OC₂H₅) | H | H | H | H | $^1$H-NMR (CDCl₃), δ=0.9 (3H, d); 1.05 (3H, t); 1.5 (1H, m); 1.9 (1H, m); 3.05 (1H, m); 3.45 (4H, m); 7.15 (2H, m); 7.35 (2H, m). |
| 44 | —cyclohexyl—OC₂H₅ | H | H | H | H | $^1$H-NMR (CDCl₃), δ= 1.05 (3H, t); 1.1–2.5 (9H, m); 3.2–3.5 (3H, m); 7.15 (2H, m); 7.30 (2H, m). |
| 45 | —CH₂—cyclohexyl | H | H | H | H | $^1$H-NMR (CDCl₃), δ= 0.8–1.8 (11H, m); 2.75 (2H, d); 7.20 (2H, m); 2.35 (2H, m). |
| 46 | —CH₂CH(OC₂H₄)₂ | H | H | H | H | $^1$H-NMR (CDCl₃), δ= 1.05 (6H, t); 3.5–3.8 (6H, m); 4.5 (2H, t); 7.15 (2H, m); 7.35 (2H, m). |
| 47 | —CH(C₂H₅)(CH₂CN) | H | H | H | H | $^1$H-NMR (CDCl₃), δ= 0.95 (3H, t); 1.50 (2H, m); 2.50 (1H, m); 2.40 (2H, d); 7.1 (2H, m); 7.3 (2H, m). |
| 48 | —cycloC₈C₁₅ | H | H | H | H | $^1$H-NMR (CDCl₃), δ= 1.2–2.0 (14H, m); 2.80 (1H, m); 7.15 (2H, m); 7.30 (2H, m). |
| 49 | —(CH₂CH₂O)₂—C₄H₉ | H | H | H | H | $^1$H-NMR (CDCl₃), δ= 0.85 (3H, t); 1.30 (2H, m); 1.50 (2H, m); 3.15 (2H, t); 3.40 (2H, m); 3.5–3.7 (6H, m); 7.15 (2H, m); 7.35 (6H, m). |
| 50 | —(CH₂CH₂O)₂CH₃ | H | H | H | H | $^1$H-NMR (CDCl₃), δ= 3.30 (3H, s); 3.3–3.9 (8H, m); 7.15 (2H, m); 7.35 (2H, m). |
| 51 | —(CH₂CH₂O)₃CH₃ | H | H | H | H | $^1$H-NMR (CDCl₃), δ= 3.15 (3H, t); 3.38 (3H, s); 3.5–3.7 (10H, m); 7.1 (2H, m); 7.3 (2H, m). |
| 52 | —(CH₂CH₂O)₃C₂H₅ | H | H | H | H | $^1$H-NMR (CDCl₃), δ= 1.22 (3H, t); 3.12 (2H, t); 3.5–3.8 (12H, m); 7.1 (2H, m); 7.35 (2H, m). |
| 53 | —CH(Ph)CO₂ᵗBu | H | H | H | H | m.p.: 132–133° C. |
| 54 | —CH(CH₂Ph)CO₂Et | H | H | H | H | $^1$H-NMR (CDCl₃), δ= 1.01 (3H); 2.98–3.27 |

TABLE 2-continued

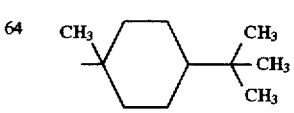

(II)

| Ex. No. | $R^1$ | $R^2$ | $R^3$ | $R^4$ | $R^5$ | Physical constants |
|---|---|---|---|---|---|---|
| 55 | —CH(i-Pr)CO$_2$Et | H | H | H | H | $^1$H-NMR (CDCl$_3$), δ= 0.94 (6H); 1.21 (3H); 2.35 (1H); 3.31 (1H); 4.03 (2H); 7.12–7.39 (4H). |
| | | | | | | (2H); 3.73 (1H); 3.90 (2H); 7.09–7.36 (9H). |
| 56 | —CH(i-Pr)CONHCH(CH$_3$)Ph | H | H | H | H | m.p.: 156.9° C. |
| 57 | —CH(CH$_3$)CO$_2$$^t$Bu | H | H | H | H | m.p.: 98° C. |
| 58 | —(CH$_2$)$_2$CO$_2$$^t$Bu | H | H | H | H | $^1$H-NMR (CDCl$_3$), δ= 1.43 (s, 9H); 2.48 (t, 2H); 3.16 (t, 2H); 7.14–7.36 (4H). |
| 59 | —CH$_2$—CO$_2$$^t$Bu | H | H | H | H | $^1$H-NMR (CDCl$_3$), δ= 1.47 (s, 9H); 3.66 (s, 2H); 7.15–7.36 (m, 4H). |
| 60 | —CH(CH$_3$)CO$_2$CH$_3$ | H | H | H | H | $^1$H-NMR (CDCl$_3$), δ= 1.37 (d, 3H); 3.60 (q, 1H); 3.70 (s, 3H); 7.13–7.34 (4H). |
| 61 | —CH(CH$_2$—CH(CH$_3$)$_2$)CO$_2$CH$_3$ | H | H | H | H | $^1$H-NMR (CDCl$_3$), δ= 0.86 (6H); 1.53 (1H); 1.67 (2H); 3.50 (1H); 3.55 (3H); 7.13–7.34 (4H). |
| 62 | —CH(i-Pr)CO$_2$$^t$Bu | H | H | H | H | $^1$H-NMR (CDCl$_3$), δ= 0.96 (6H); 1.39 (9H); 3.19 (1H); 7.12–7.32 (4H). |
| 63 | —C(CH$_3$)$_2$—CH$_2$—C(CH$_3$)$_3$ | H | H | H | H | $^1$H-NMR (CDCl$_3$), δ= 1.00 (9H); 1.04 (6H); 1.58 (2H); 7.05–7.28 (4H). |
| 64 | ![cyclohexyl-C(CH3)3 group] | H | H | H | H | m.p.: 178° C. |
| 65 | —C(CH$_3$)$_2$—(CH$_2$)$_5$C(CH$_3$)$_3$ | H | H | H | H | $^1$H-NMR (CDCl$_3$), δ= 0.60–1.60 (25H); 7.08 (2H); 7.25 (2H). |

Use Example:

In order to demonstrate the activity against fungi, the minimum inhibitory concentrations (ICs) of compositions according to the invention are determined:

An agar prepared using malt extract is treated with active compounds according to the invention in concentrations of from 0.1 mg/l to 5000 mg/l. After solidification of the agar, it is contaminated with pure cultures of the test organisms listed in Table 1. After storage at 28° C. and 60 to 70% relative atmospheric humidity for 2 weeks, the MIC is determine. The MIC is the lowest concentration of active compound at which the species of microbe used shows no growth, and is indicated in Table 3 below.

TABLE 3

| Compound | MIC/ppm Penicillin brevicule | MIC/ppm Chaetomium globosum | MIC/ppm Aspergillus niger |
|---|---|---|---|
| 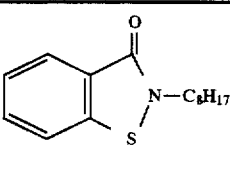 | >600 | >100 | >600 |
| 1 | <600 | <100 | <600 |

We claim:

1. A method of protecting industrial materials against microbes which comprises applying thereto a microbicidally effective amount of 1,3,2-benzodithiazol-1-oxides of the formula (I)

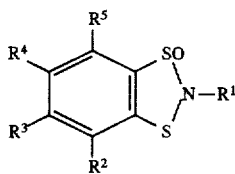

in which
- $R^1$ represents hydrogen, straight-chain or branched alkyl having 1 to 18 carbon atoms, straight-chain or branched alkenyl having 2 to 18 carbon atoms or straight-chain or branched alkinyl having 2 to 18 carbon atoms, the above recited alkyl, alkenyl and alkinyl being optionally substituted one or more times by identical or different substituents consisting of halogen, alkoxy having 1 to 6 carbon atoms, halogenoalkoxy having 1 to 6 carbon atoms and 1 to 9 identical or different halogen atoms, alkilthio having 1 to 6 carbon atoms, halogenoalkylthio having 1 to 6 carbon atoms and 1 to 9 identical or different halogen atoms, carboxylic acid acyl having 1 to 6 carbon atoms, carboxylic acid acyloxy having 1 to 6 carbon atoms, (alkoxy)-carbonyl having 1 to 6 carbon atoms, amino which is optionally substituted by identical or different substituents consisting of alkyl or aryl optionally substituted phenoxy or pyridyloxy, nitro or cyano;
- or represents cycloalkyl consisting of 1 to 4 interconnected ring systems having 3 to 18 carbon atoms which is optionally substituted one or more times by identical or different substituents consisting of halogen, alkyl having 1 to 4 carbon atoms, halogenoalkyl having 1 to 4 carbon atoms and 1 to 5 identical or different halogen atoms, alkoxy having 1 to 4 carbon atoms, halogenoalkoxy having 1 to 4 carbon atoms and 1 to 5 identical or different halogen atoms, alkylthio having 1 to 4 carbon atoms, halogenoalkylthio having 1 to 4 carbon atoms and 1 to 5 identical or different halogen atoms, nitro or cyano;
- or represents carbocycle aryl which is optionally substituted from one to five times by halogen, alkyl having 1 to 10 carbon atoms, halogenoalkyl having 1 to 8 carbon atoms and 1 to 8 identical or different halogen atoms, alkoxy having 1 to 10 carbon atoms, halogenalkoxy having 1 to 8 atoms and 1 to 8 identical or different halogen atoms, alkylthio having 1 to 10 carbon atoms, halognalkylthio having 1 to 8 carbon atoms and 1 to 8 identical or different halogen atoms, amino, monoalkylamino having straight-chain or branched alkyl radicals having 1 to 6 carbon atoms, dialkylamino having identical or different, straight-chain or branched alkyl radicals each having 1 to 6 carbon atoms, cycloalkyl having 1 to 6 carbon atoms, difluoromethylenedioxy, chlorofluoromethylenedioxy, dichlorotnethylenedioxy, nitro or cyano;
- or represents carbocyclic aralkyl in which the alkyl radical is straight or branched and consists of 1 to 8 carbon atoms and aryl represents phenyl which is optionally substituted from one to four times by identical of different substituents consisting of halogen, alkyl having 1 to 6 carbon atoms, halogenoalkyl having 1 to 6 carbon atoms and 1 to 6 identical or different halogen atoms, alkoxy having 1 to 6 on atoms, halogenoalkoxy having 1 to 6 carbon atoms and 1 to 6 identical or different halogen atoms, alkylthio having 1 to 6 carbon atoms, halogenoalkylthio having 1 to 6 carbon atoms and 1 to 6 identical or different halogen atoms, amino, monoalkylamino having straight-chain or branched alkyl radicals having 1 to 6 carbon atoms, diallylamino having identical or different, straight-chain or branched alkyl radicals each having 1 to 6 carbon atoms, cycloalkyl having 1 to 6 carbon atoms, methylenedioxy, difluoromethylenedioxy, chlorofluoromethylenedioxy, dichloromethylenedioxy, nitro or cyano;
- $R^2$, $R^3$, $R^4$ and $R^5$ each independently of one another represent hydrogen, halogen, alkyl having 1 to 6 carbon atoms, halogenoalkyl having 1 to 6 carbon atoms and 1 to 6 identical or different halogen atoms, alkoxy having 1 to 6 carbon atoms, halogenoalkoxy having 1 to 6 carbon atoms and 1 to 6 identical or different halogen atoms, alkylthio having 1 to 6 carbon atoms, halogenoalkylthio having 1 to 6 carbon atoms and 1 to 6 identical or different halogen atoms, dialkylamino having identical or different, straight-chain or branched alkyl radicals each having 1 to 6 carbon atoms, nitro cyano.

2. A method according to claim 1, wherein compounds of the formula (I) are employed in which
- $R^1$ represents hydrogen, straight-chain or branched alkyl having 1 to 14 carbon atoms, straight-chain or branched alkenyl having 2 to 14 carbon atoms or straight-chain or branched alkinyl having 2 to 14 carbon atoms, the above recited alkyl, alkenyl and alkinyl being substituted from one to four times by identical or different substituents consisting of fluorine, chlorine, alkoxy having 1 to 5 carbon atoms, halogenoalkoxy having 1 to 5 carbon atoms and 1 to 5 fluorine and/or chlorine atoms, alkylthio having 1 to 5 carbon atoms, halogenoalkylthio having 1 to 5 carbon atoms and 1 to 5 fluorine and/or chlorine atoms, carboxylic acid acyl having 1 to 5 carbon atoms, carboxylic acid acyloxy having 1 to 5 carbon atoms, alkoxycarbonyl having 1 to 5 carbon atoms, amino which is optionally substituted by identical or different substituents consisting of alkyl having 1 to 4 carbon atoms and/or phenyl, phenoxy or pyridyloxy, nitro or cyano;
- or represents cyrloalkyl consisting of 1 to 3 ring systems having 3 to 14 carbon atoms which is optionlly substituted from one to four times by identical or different substituents consisting of fluorine/chlorine, alkyl having 1 to 4 carbon atoms, alkoxy having 1 to 4 carbon atoms, alkylthio having 1 to 4 carbon atoms, nitro or cyano;
- or represents carbocyclic aryl which is optionally substituted from one to four times by fluorine, chlorine, alkyl having 1 to 8 carbon atoms, halogenoalkyl, having 1 to 6 carbon atoms and 1 to 6 flourine and/or chlorine atoms, alkoxy having 1 to 8 carbon atoms, halogenalkoxy having 1 to 6 carbon atoms and 1 to 6 fluorine and/or chlorine atoms, alkylthio 1 to 8 carbon atoms, halogenoalkylthio having 1 to 6 carbon atoms and 1 to 6 fluorine and/or chlorine atoms, amino, monoalkylamino having alkyl radicals of 1 to 4 carbon atoms, dialkylamino having identical or different alkyl radicals each having 1 to 4 carbon atoms, cycloalkyl having 1 to 6 carbon atoms, difluoromethylenedioxy, chlorofluoromethyloedioxy, dichloromethylenedioxy, nitro or cyano;

or represents carbocyclic aralkyl in which the alkyl radical is straight chain or branched and consists of 1 to 8 carbon atoms and aryl represents phenyl which is optionally substituted from one to four times by fluorine, chlorine, alkyl having 1 to 4 carbon atoms, halogenoalkyl having 1 to 4 carbon atoms and 1 to 4 flourine and/or chlorine atoms, alkyl having 1 to 4 atoms, halogenoalkoxy having 1 to 4 carbon atoms and 1 to 4 fluorine and/or chlorine atoms, alkylthio having 1 to 4 carbon atoms, halogenoalkylthio having 1 to 4 carbon atoms and 1 to 4 flourine and/or chlorine atoms, amino, monoalkylamino having alkyl radicals of 1 to 4 carbon atoms, dialkylamino having identical or different alkyl radicals each having 1 to 4 carbon atoms, cycloalkyl having 1 to 6 carbon atoms, methylenedioxy, difluoromethylenedioxy, chlorofluoromethylenedioxy, dichloromethylenedioxy, nitro or cyano;

$R^2$, $R^3$, $R^4$ and $R^5$ each independently of one another represent hydrogen, chlorine, fluorine, alkyl having 1 to 4 carbon atoms, halogenoalkyl having 1 to 4 carbon atoms and 1 to 6 fluorine and/or chlorine atoms, alkoxy having 1 to 4 carbon atoms, halogenoalkyl having 1 to 4 carbon atoms and 1 to 6 fluorine and/or chlorine atoms, alkylthio having 1 to 4 carbon atoms, halogenoalkylthio having 1 to 4 carbon atoms 1 to 6 fluorine and/or chlorine atoms, dialkylamino having identical or different, straight-chain or branched alkyl radicals each having 1 to 6 carbon atoms, nitro or cyano.

3. A method according to claim 1, wherein the 1,3,2-benzodiothiazol-1-oxides are applied in combination with a diluent.

* * * * *